United States Patent [19]

Shibuya et al.

[11] 4,229,573
[45] Oct. 21, 1980

[54] 7α-METHOXYCEPHALOSPORIN DERIVATIVES

[75] Inventors: Chisei Shibuya; Hirataka Itoh; Kunihiko Ishii; Torao Ishida; Mitsuru Shibukawa, all of Fuji, Japan

[73] Assignee: Asahi Kasei Kogyo Kabushiki Kaisha, Osaka, Japan

[21] Appl. No.: 808,631

[22] Filed: Jun. 21, 1977

[51] Int. Cl.$^2$ ............................................. C07D 501/20
[52] U.S. Cl. .................................... 544/21; 424/246
[58] Field of Search ........................................... 544/21

[56] References Cited

U.S. PATENT DOCUMENTS

| | | | |
|---|---|---|---|
| 3,382,238 | 5/1968 | Dolfini | 260/243 C |
| 3,516,997 | 6/1970 | Takano et al. | 544/27 |
| 3,865,819 | 2/1975 | Demarinis et al. | 260/243 C |
| 3,880,848 | 4/1975 | Demarinis et al. | 260/243 C |
| 3,948,905 | 4/1976 | Demarinis et al. | 544/26 |
| 4,005,081 | 1/1977 | Miyadera et al. | 544/21 |
| 4,007,177 | 2/1977 | Nakao et al. | 544/21 |
| 4,026,886 | 5/1977 | Dolfini et al. | 544/21 |
| 4,048,311 | 9/1977 | Berges | 544/21 |

FOREIGN PATENT DOCUMENTS 2558869  1/1976  Fed. Rep. of Germany .
2539411  4/1976  Fed. Rep. of Germany .

OTHER PUBLICATIONS

Fieser et al., Organic Chemistry, pp. 267–270, (1950).

*Primary Examiner*—Nicholas S. Rizzo
*Attorney, Agent, or Firm*—Cushman, Darby & Cushman

[57] ABSTRACT

Novel 7α-methoxycephalosporin derivatives having a high antimicrobial activity. They are useful for the medical treatment of diseases infected by gram-positive bacteria and gram-negative bacteria. More particularly, they show an antimicrobial activity against bacteria such as *Eschericha coli* Proteus, Citrobacter and Enterobacter which bacteria have resistance to the conventionally employed cephalosporins, and they are effective for the medical treatment of diseases infected by these bacteria. Such 7α-methoxycephalosporin derivatives are prepared by a relatively simple method.

10 Claims, No Drawings

7α-METHOXYCEPHALOSPORIN DERIVATIVES

The present invention relates to novel 7α-methoxycephalosporin derivatives and their pharmacologically acceptable salts and esters, which are each useful as an antimicrobial agent, and a process for preparing the same.

It is an object of this invention to provide novel 7α-methoxycephalosporin derivatives and their pharmacologically acceptable salts and esters each having a high antimicrobial activity.

Another object of this invention is to provide a process for preparing these 7α-methoxycephalosporin derivatives and their pharmacologically acceptable salts and esters each having a high antimicrobial activity.

As a result of our intensive and extensive researches with a view to developing novel cephalosporin derivatives having a high antimicrobial activity, it has been found that 7α-methoxycephalosporin derivatives of the following general formula (I) and of the R form in the sulfinyl group in the general formula (I), and their pharmacologically acceptable salts and esters, have a high antimicrobial activity:

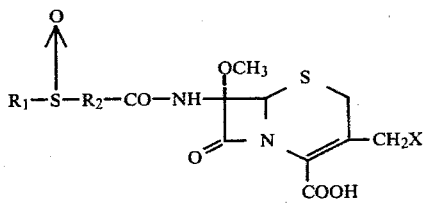

wherein
- $R_1$ stands for a lower alkyl group, a lower alkynyl group, an aryl group, an aralkyl group, a heterocyclic group or a heterocyclic-lower alkyl group, said groups each being unsubstituted or substituted with at least one member selected from the group consisting of halogen, nitro, hydroxy, lower alkenyl, lower alkoxy, azido, amino, substituted amino, carboxy, carboxy-lower alkyl, trifluoromethyl, cyano, ureido, mercapto, carbamoyl, sulfinyl, sulfonyl, hydrazino, formyl, acetoxy, amino-lower acyl, amino-lower alkyl, lower acyl, carbonyl, thio, hydroxyamino, lower alkyl, hydroxy lower alkyl, lower alkoxymethyl, N-oxo, carbo-lower alkoxy and thiocarbonyl;
- $R_2$ stands for a 1 to 3 carbon atom straight chain alkylene group unsubstituted or substituted with methyl; and
- X stands for a hydrogen atom, an acetoxy group, a quaternary ammonium group, a carbamoyloxy group, a lower alkoxy group, a lower alkylmercapto group or a heterocyclic-mercapto group, said heterocyclic-mercapto group being unsubstituted or substituted with at least one member selected from the same group of substitutents as defined in the definition of $R_1$;

wherein said R form means an optical isomer having stereochemically the same structure in the sulfinyl group as that optical isomer of the two sulfinyl group stereoisomers of a compound of the general formula (II) which has a positive specific rotation in ethanol:

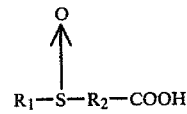

wherein $R_1$ and $R_2$ are the same as defined above.

The compound represented by the above general formula (II) is asymmetric in the sulfinyl group and includes two optical isomers. Accordingly, 7α-methoxycephalosporins derived from this compound include two kinds of optical isomers in the sulfinyl group. Between two kinds of optical isomers of 7α-methoxycephalosporins, the intended isomer of the present invention is one derived from that optical isomer of the two sulfinyl group stereoisomers of a compound of the above general formula (II) which has a positive specific rotation in ethanol.

Compounds of the present invention have an antimicrobial activity and are therefore useful for the medical treatment of many diseases infected by gram-positive bacteria and gram-negative bacteria. More particularly, it should be noted that since the compounds of the present invention shown an antimicrobial activity against bacteria such as *Escherichianoli Citrobacter* and *Enterobacter* which bacteria have resistance to the conventionally employed cephalosporins, they are effective for the medical treatment of diseases infected by these bacteria, such as diseases of hepatic bile, e.g. cholecystitis, diseases of blood, e.g. septicemia, and diseases of urinary passage, e.g. nephropyelitis. The compounds of the present invention are also useful as a bactericide and an animal feed supplement.

In compounds of the present invention, a 7-methoxy group holds the α-configuration.

Definitions of respective symbols in the aforementioned general formula (I) will now be described.

By the lower alkyl group is meant a straight chain or branched aliphatic hydrocarbon group having 1 to 8 carbon atoms. Specific examples of lower alkyl groups include, methyl, ethyl, propyl, isopropyl, n-butyl, isobutyl, t-butyl, amyl and the like.

By the lower alkynyl group is meant a straight chain or branched aliphatic hydrocarbon group having 2 to 8 carbon atoms and one triple bond. Specific examples of lower alkynyl groups include ethynyl, propargyl and the like.

By the aryl group is meant a mono- and carbo- cyclic aryl group having no substituent or having 1 to 3 substituents, i.e., a phenyl group or a substituted phenyl group having 1 to 3 substituents. As examples of the substituents, there can be mentioned a halogen atom, a lower alkyl group as defined above, a lower alkoxy group (a group consisting of a lower alkyl group as defined above and an oxygen atom bonded to said lower alkyl group), a hydroxyl group, a cyano group, a carboxyl group, a nitro group, an amino group, a di(lower alkyl) amino group (an amino group substituted with two lower alkyl group as defined above), an amino-lower alkyl group (a group consisting of a lower alkyl group as defined above and an amino group bonded to said lower alkyl group) and the like. Specific examples of aryl groups include phenyl, o-, m- and p- chlorophenyls, o-, m- and p- bromophenyls, 3,4-dichlorophenyl, 3,5-dibromophenyl, o-, m- and p- tolyls p-methoxyphenyl, 3,4,5-trimethoxyphenyl, p-hydroxyphenyl, o-, m- and p- carboxyphenyls, 2-aminomethylphenyl and the like.

By the aralkyl group is meant a group consisting of a lower alkyl group as defined above and a mono- and carbocyclic aryl group as defined above which is bonded to said lower alkyl group. Specific examples of aralkyl groups include benzyl, o-, m- and p- chlorobenzyls, o-, m-, and p-methylbenzyls, phenethyl, p-chlorophenethyl, 3,5-diethylbenzyl, 3,4,5-trichlorobenzyl and the like.

By the heterocyclic group is meant a heterocyclic group which is a mono- or bi-cyclic ring residue containing in at least one ring 1 to 4 hetero atoms selected from the group consisting of nitrogen, oxygen and sulfur, the or each said ring being a 5- or 6-membered one. Specific examples of heterocyclic groups include pyridyl, 1-oxopyridyl, pyrimidyl, 2-oxopyrimidyl, 2-thionpyrimidyl, 2-oxo-5-methyl-pyrimidyl, pyridazinyl, 1- and 2-oxo-5-pyridizinyls, thienyl, pyrazolyl, diazolyl, triazolyl, tetrazolyl, oxadiazolyl, thiadiazolyl, 6-oxopurinyl, uracil, furyl, imidazolyl, oxazolyl, thiazolyl, benzimidazolyl and the like. The above-defined heterocyclic group may be substituted with at least one member selected from the same group of substituents as defined in the definition of $R_1$ in the general formula (I).

By the lower acyl residue of a lower fatty acid containing a lower alkyl group as defined above. Specific examples of lower acyl include acetyl, propionyl and the like.

By the lower alkenyl is meant a straight chain or branched aliphatic hydrocarbon group having 2 to 8 carbon atoms and one double bond. Specific examples of lower alkenyl groups include allyl, isopropenyl, pentenyl and the like.

By the substituted amino is meant an amino group substituted with one or two lower alkyl groups as defined above. Specific examples of substituted amino include monomethylamino, dimethylamino and the like.

By the lower alkoxy group is meant a group consisting of a lower alkyl group as defined above and an oxygen atom bonded to said lower alkyl group. Specific examples of lower alkoxy groups include methoxy, ethoxy and the like.

As examples of a quaternary ammonium group, there can be mentioned N,N'-dibenzylpyridinium, pyridinium, 1-quinolinium, 1-picolinium and the like.

By the lower alkylmercapto group is meant a group consisting of a lower alkyl group as defined above and a sulfur atom bonded to said lower alkyl group. Specific examples of lower alkylmercapto groups include mercapto groups each substituted with a lower alkyl group such as methyl, ethyl, propyl, pentyl or the like.

By the heterocyclic-mercapto group is meant a group consisting of a heterocyclic group as defined above and a sulfur atom bonded to said heterocyclic group. Specific examples of heterocyclic-mercapto groups include mercapto groups each substituted with a heterocyclic group such as pyridyl, 1-oxopyridyl, pyrimidyl, 2-oxopyrimidyl, 2-thionpyrimidyl, 2-oxo-5-methylpyrimidyl, pyridazinyl, 1- or 2-oxo-5-pyridazinyl, thienyl, pyrazolyl, diazolyl, triazolyl, tetrazolyl, oxadiazolyl, thiadiazolyl, 6-oxopurinyl, uracil or the like. The above-mentioned heterocyclic groups may be substituted with at least one member selected from the same group of substituents as defined in the definition of $R_1$ in the general formula (I).

Further according to the present invention, there is provided a process for preparing a 7α-methoxycephalosporin of the formula (I) and of the R form in the sulfinyl group, or its pharmacologically acceptable salts or esters:

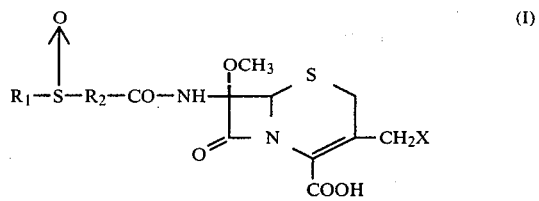

wherein
$R_1$ stands for a lower alkyl group, a lower alkynyl, group, an aryl group, an aralkyl group, a heterocyclic group or a heterocyclic-lower alkyl group, said groups each being unsubstituted or substituted with at least one member selected from the group consisting of halogen, nitro, hydroxy, lower alkenyl, lower alkoxy, azido, amino, substituted amino, carboxy, carboxy-lower alkyl, trifluoromethyl, cyano, ureido, mercapto, carbamoyl, sulfinyl, sulfonyl, hydrazino, formyl, acetoxy, amino-lower acyl, amino-lower alkyl, lower acyl, carbonyl, thio, hydroxyamino, lower alkyl, hydroxy-lower alkyl, lower alkoxymethyl, N-oxo, carbo-lower alkoxy and thiocarbonyl;
$R_2$ stands for a 1 to 3 carbon atom straight chain alkylene group unsubstituted or substituted with methyl;
X stands for a hydrogen atom, an acetoxy group, a quaternary ammonium group, a carbamoyloxy group, a lower alkoxy group, a lower alkylmercapto group or a heterocyclic-mercapto group, said heterocyclic-mercapto group being unsubstituted or substituted with at least one member selected from the same group of substituents as defined in the definition of $R_1$; and
wherein said R form means an optical isomer having stereochemically the same structure in the sulfinyl group as that optical isomer of the two sulfinyl group stereoisomers of a compound of the formula (II) which has a positive specific rotation in ethanol:

wherein $R_1$ and $R_2$ are the same as defined above; characterized in that
a compound of the formula (III)

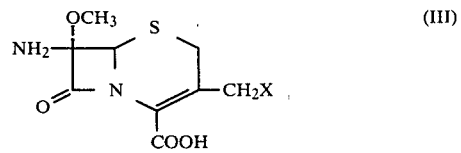

wherein
X is the same as defined above, or a protected ester compound thereof is reacted with a compound of the formula (II) and of the R form or of the racemic form, or its reactive derivative, and in case the protected ester compound of a 7α-methoxycephalosporin of the formula (I) and of the R form or of the racemic form is synthesized, the protective group is removed, if desired, to obtain the corresponding free acid;

and optionally the obtained 7α-methoxycephalosporin of the formula (I) is reacted with a pharmacologically acceptable salt- or ester-forming agent;

in case a 7α-methoxycephalosporin of the formula (I) and of the racemic form or its pharmacologically acceptable salt or ester is synthesized, the corresponding R form being separated by a method as known per se.

Still further according to the present invention, there is provided a process of the kind described above, characterized in that in case the 7α-methoxycephalosporin of the R form or of the racemic form obtained is a compound of the formula (I) wherein $R_1$ and $R_2$ are the same as defined above and X is an acetoxy group or a carbamoyloxy group, or a protected ester compound thereof, said compound or said protected ester compound is further reacted with a nitrogen-containing compound capable of substituting said acetoxy group or said carbamoyloxy group to cause X to be converted into a quaternary ammonium group, or with a mercapto compound capable of substituting said acetoxy group or said carbamoyloxy group to cause X to be converted into a lower alkylmercapto group or an unsubstituted or substituted heterocyclic-mercapto group, to obtain a 7α-methoxycephalosporin of the R form or of the racemic form and of the formula (I) wherein $R_1$ and $R_2$ are the same as defined above and X is a quaternary ammonium group, a lower alkylmercapto group or an unsubstituted or substituted heterocyclic-mercapto group, or a protected ester compound thereof, and in case the obtained protected ester compound of a 7α-methoxycephalosporin of the R form or of the racemic form and of the formula (I) wherein $R_1$ and $R_2$ are the same as defined above and X is a quaternary ammonium group, a lower alkylmercapto group or an unsubstituted or substituted heterocyclic-mercapto group is synthesized, the protective group is removed, if desired, to obtain the corresponding free acid;

and optionally the obtained 7α-methoxycephalosporin of the formula (I) wherein $R_1$ and $R_2$ are the same as defined above and X is a quaternary ammonium group, a lower alkylmercapto group or an unsubstituted or substituted heterocyclic-mercapto group is reacted with a pharmacologically acceptable salt- or ester-forming agent;

in case a 7α-methoxycephalosporin of the racemic form and of the formula (I) wherein $R_1$ and $R_2$ are the same as defined above and X is a quaternary ammonium group, a lower alkylmercapto group or an unsubstituted or substituted hererocyclic-mercapto group, or its pharmacologically acceptable salt or ester is synthesized, the corresponding R form being separated by a method as known per se.

As described above, one example of methods for preparing the intended compound of the present invention will be explained as follows.

A compound of the following formula (II) and of the R form in the sulfinyl group:

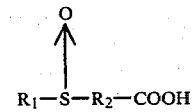

wherein $R_1$ and $R_2$ are the same as defined above, or its reactive derivative is reacted with a compound represented by the following formula (III):

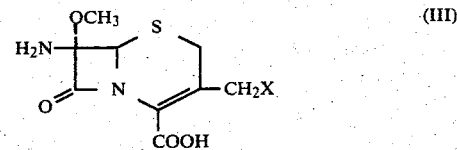

wherein X is the same as defined above, or its protected ester compound to obtain a compound represented by the above general formula (I) or its protected ester compound. The protective group of the obtained protected ester compound may be removed if desired.

As a carboxyl-protecting group for a compound represented by the above formula (III), any group can be used for this purpose without any restriction of the kind so far as it is one usually used in the field of this art and having such a tendency that it is easily cleaved. Specific examples of carboxyl-protecting groups to be preferably used in the present invention include a benzhydryl group, a benzyl group, a p-methoxybenzyl group, a t-butyl group, a benzyloxymethyl group, a methoxymethyl group, a phenacyl group, a p-bromophenacyl group, a 2,2,2-trichloroethyl group and the like. A benzyhydryl group is especially preferred.

Preferred examples of the group X in a compound represented by the above formula (III) and to be used as a starting compound in the present invention include hydrogen, acetoxy, methoxy, methylthio, 1H-tetrazol-5-ylthio, 1-methyl-1H-tetrazol-5-ylthio, 1-ethyl-1H-tetrazol-5-ylthio, 1,3,4-thiadiazol-2-ylthio, 5-methyl-1,3,4-thiadiazol-2-ylthio, 1,3,4-oxadiazol-2-ylthio, 5-methyl-1,3,4-oxadiazol-2-ylthio, 1H-1,3,4-triazol-2-ylthio, 5-methyl-1H-1,3,4-triazol-2-ylthio, 1-ethyl-1H-1,3,4-triazol-2-ylthio, 1H-1,2,3-triazol-5-ylthio, 1-methyl-1H-1,2,3-triazol-5-ylthio, 1-methyl-1H-1,3,4-triazol-2-ylthio, 3-methyl-1,2,4-thiadiazol-5-ylthio, 1-pyridinium, carbamoyloxy, N-oxopyridin-2-ylthio, -carboxymethyl-1H-tetrazol-5-ylthio and 6-methyl-1-oxopyridazin-3-ylthio. Acetoxy, carbamoyloxy, 1-methyl-1H-tetrazol-5-ylthio and 5-methyl-1,3,4-thiadiazol-2-ylthio are especially preferred.

In the method of the present invention, the reaction between the compound of the formula (II) and the compound of the formula (III) is usually carried out in a suitable inactive solvent. Any solvent can be used without any restriction of the kind so far as it does not take part in the above-mentioned reaction. Preferred examples of suitable solvents to be used in the reaction include chloroform, methylene chloride, ethylene chloride, acetone, dioxane, acetonitrile, tetrahydrofuran, ethyl acetate, ethyl formate, ethers and the like. Among these solvents, water-soluble ones may be used in mixture with water.

As preferred examples of carboxylic acids of the R form represented by the general formula (II) and to be used in the present invention, there can be mentioned methylsulfinylacetic acid, ethylsulfinylacetic acid, 2- methylsulfinylpropionic acid, 3-methylsulfinylpropionic acid, trifluoromethylsulfinylacetic acid, 2,2,2-trifluoroethylsulfinylacetic acid, n-propylsulfinylacetic acid, cyanomethylsulfinylacetic acid, propargylsulfinylacetic acid, azidomethylsulfinylacetic acid, 3-ethylsulfinylpropionic acid, 2-ethylsulfinyl-2-methylpropionic acid, 2-methyl-2-methylsulfinylpropionic acid, 3-phenylsulfinylpropionic acid, 3-benzylsulfinylpropionic acid, 2-ethylsulfinyl-2-methylpropionic acid, 3-benzylsulfinylbutyric acid, 2-methyl-2-phenethylsulfinylpropionic acid, cyanomethylsulfinylpropionic acid, phenylsulfinylacetic acid, 4-hydroxyphenylsulfinylacetic acid, 4-aminosulfonylphenylsulfinylacetic acid, 2-aminomethylphenylsulfinylacetic acid, 4-chlorophenylsulfinylacetic acid, 2-carboxyphenylsulfinylacetic acid, 2-thienylsulfinylacetic acid, 3-thienylsulfinylacetic acid, 4-pyridylsulfinylacetic acid, 2-pyridylsulfinylacetic acid, 3-pyridylsulfinylacetic acid, N-methyl-4-pyridylsulfinylacetic acid, N-oxo-4-pyridylsulfinylacetic acid, 5-methyl-1,3,4-thiadiazol-2-ylsulfinylacetic acid, 1,3,4-thiadiazol-2-ylsulfinylacetic acid, 3-methyl-1,2,4-thiadiazol-5-ylsulfinylacetic acid, 1-methyl-1H-tetrazol-5-ylsulfinylacetic acid, 1,3,4-triazol-5-ylsulfinylacetic acid, 1,2,3-triazol-5-ylsulfinylacetic acid, 1-methyl-1,2,3-triazol-5-ylsulfinylacetic acid, 2-phenyl-1,3,4-triazol-5-ylsulfinylacetic acid, imidazol-2-ylsulfinylacetic acid, isoxazol-3-ylsulfinylacetic acid, pyridazin-3-ylsulfinylacetic acid, 1-oxopridazin-3-ylsulfinylacetic acid, benzimidazol-2-ylsulfinylacetic acid, 2-thienylmethylsulfinylacetic acid, 2-furylsulfinylacetic acid, benzothiazol-2-ylsulfinylacetic acid and the like. These carboxylic acids of the R form can be prepared by the following procedures. A carboxylic acid having a thio group in place of a sulfinyl group of an intended carboxylic acid is oxidized with, for example hydrogen peroxide to obtain the sulfinyl group-containing carboxylic acid. The thus obtained carboxylic acid is optically resolved with a optically resolving agent such as brucine, cinchonine, cinchonidine or the like to obtain the intended carboxylic acid of the R form.

As the reactive derivatives of the carboxylic acid of the R form represented by the above formula (II), there can be mentioned carboxylic acid derivatives such as acid halides, mixed acid anhydrides, an acid anhydride, active amides, an acid azide and the like. As examples of acid halides, there can be mentioned halides of the above-mentioned carboxylic acid, such as a chloride, a bromide and the like. As examples of mixed acid anhydrides, there can be mentioned anhydrides between the above-mentioned carboxylic acid and acids such as alkylphosphoric acids, alkylcarbonic acids, aliphatic carboxylic acids and the like. An example of the active amides is an amide derived from the above-mentioned carboxylic acid and triazole.

In case a reactive derivative of a carboxylic acid of the R form represented by the above general formula (II) is used, the reaction between said reactive derivative and a compound represented by the above general formula (III) or its protected ester compound is conducted in the aforementioned inactive solvent at a temperature of −50° to 100° C. for several minutes to several tens of hours to obtain a 7α-methoxycephalosporin of the R form represented by the above general formula (I) or its protected ester compound. The mole ratio of amounts of both reactants to be used in the reaction may be preferably 1:2 to 2:1.

In case a carboxylic acid of the R form represented by the above general formula (II) is used, the reaction between both reactants is conducted in the presence of N,N'-dicyclohexylcarbodiimide, N,N'-diethylcarbodiimide, diphenylphosphoric acid azide, diethylphosphoric acid cyanide, hexachlorocyclotriphosphatriazine, triazine trichloride or the like. The reaction is conducted at −50° to 100° C. for several minutes to several tens of hours. The mole ratio of amounts of both reactants may be preferably 1:2 to 2:1.

In general, the reaction temperature in the process of this invention is not critical, but the reaction is conducted at about −50° C. to 100° C., preferably at −20° C. to room temperature. The reaction time also is not critical and it may be varied, for example, from several minutes to several tens of hours, depending on the kind and type of starting material and reaction solvent employed, the reaction temperature applied and other factors.

The so obtained 7α-methoxycephalosporin of the R form or its protected ester compound is isolated from the reaction mixture by an ordinary method. For example, the reaction mixture is washed with water and the solvent used in the reaction is distilled off to obtain the residue of the desired compound. In case the purity of the residue is still insufficient, the residue is further purified by chromatography or the like.

In case the product of the above-mentioned reaction is a protected ester, for example benzhydryl ester, p-methoxybenzyl ester or 2,2,2-trichloroethyl ester, of a compound of the R form represented by the above general formula (I), the protected ester compound is subjected to an ordinary treatment for removal of the protective group to be converted into the intended compound of the R form represented by the above general formula (I). The removal of the protective group is conducted by reduction or acid treatment. As a reduction method, not only chemical reduction but also catalytic reduction may be employed in the present invention. But it is preferred to employ chemical reduction which is conducted using, for example, a combination of a metal such as zinc and an acid such as acetic acid. On the other hand, it is a practical mode of an acid treatment for removal of the protective group that an acid such as trifluoroacetic acid or the like is contacted in the presence or the absence of a suitable solvent with the protected ester compound of the compound represented by the above general formula (I). Although the kind of an acid to be used is not especially restricted, trifluoroacetic acid is preferred. As a solvent to be used in the reaction of the acid treatment, any solvent can be used without any restriction of the kind so far as it does not take part in the reaction. Examples of suitable solvents include halogenated aliphatic hydrocarbons such as chloroform and dichloromethane, unsubstituted and substituted aromatic hydrocarbons such as benzene, toluene, chlorobenzene and anisole, and the like. Anisole is usually the most preferred solvent. The reaction temperature is not critical, but it is preferred to conduct the reaction at a relatively low temperature, usually at 0° to 30° C. so that the intended compound may be obtained in good yield. The reaction time may be varied depending mainly on the kinds of a protective group, an acid and a solvent and the reaction temperature. But it is usually around several tens of minutes which is enough for completion of the reaction. After completion of the reaction, the reaction product, i.e., the intended compound of the R form represented by the above general formula (I) is isolated from the reaction mixture by an ordinary method. For example, the reaction mixture is subjected to extraction with an aqueous solution of a weak base, e.g. dipotassium hydrogenphosphate. The extract is then acidified and further subjected to extraction with a suitable solvent. The solvent in the extract is distilled off to obtain the residue of the intended compound.

As another method for preparing a compound of the present invention, there is a method in which a compound of the R form represented by the above general formula (I) wherein X is an acetoxy group or a carbamoyloxy group in this case is synthesized and then reacted with a nitrogen-containing compound capable of substituting said acetoxy group or said carbamoyloxy group to cause X to be converted into a quaternary ammonium group, or with a mercapto compound capable of substituting said acetoxy group or said carbamoyloxy group to cause X to be converted into a lower alkylmercapto group or an unsubstituted or substituted heterocyclic-mercapto group. Such a mercapto compound may be used in the form of free acid but is also employed in the form of an alkali metal salt thereof, such as a sodium salt or a potassium salt thereof.

The reaction according to this method may advantageously be carried out in a solvent, such as water or a mixed solvent of water and an organic solvent which can be readily mixed with water and is inactive to the starting compound as represented by the formula (I) wherein $R_1$ and $R_2$ are the same as defined above and X is an acetoxy group or a carbamoyloxy group. Preferred examples of suitable solvents to be used in the reaction include dimethylformamide, dimethylacetamide, dioxane, acetone, alcohols, acetonitrile, dimethylsulfoxide, tetrahydrofuran and the like. The ratio of the compound to be substituted for X to the above starting compound may be preferably 1:1 to 2:1. Though reaction conditions such as a reaction temperature and time are varied depending on the starting materials and solvent employed, the reaction temperature and the reaction time may generally be in the range of 0° to 100° C. and in the range of several tens of minutes to several tens of hours, respectively. The reaction may be carried out at pH 2 to 8 and advantageously at pH 5 to 8.

As still another method for preparing a compound of the present invention, there is a method in which a compound of the above general formula (I) and of the racemic form in the sulfinyl group is synthesized and the corresponding 7α-methoxycephalosporin of the R form is then separated by, for example, recrystallization or reversed phase chromatography.

Specific examples of compounds of the R form represented by the above general formula (I) according to the present invention are as follows:

7β-(methylsulfinylacetamido)-7α-methoxy-3-acetoxymethyl-3-cephem-4-carboxylic acid and its analogous compounds which have, in place of the methylsulfinyl, their respective substituents such as trifluoromethylsulfinyl, 2,2,2-trifluoroethylsulfinyl, cyanomethylsulfinyl, n-propylsulfinyl, propargylsulfinyl, azidomethylsulfinyl, phenylsulfinyl, 4-hydroxyphenylsulfinyl, 4-chlorophenylsulfinyl, 2-thienylsulfinyl, 3-thienylsulfinyl, 2-carboxyphenylsulfinyl, 4-pyridylsulfinyl, N-oxo-4-pyridylsulfinyl, 5-methyl-1,3,4-thiadiazol-2-ylsulfinyl, 1,3,4-thiadiazol-2-ylsulfinyl, 1-methyl-1H-tetrazol-5-ylsulfinyl, 1,3,4-triazol-5-ylsulfinyl, 1,2,3-triazol-5-ylsulfinyl, 1-methyl-1,2,3-triazol-5-ylsulfinyl, pyridazin-3-ylsulfinyl, 2-thienylmethylsulfinyl, 2-furylsulfinyl, 1-oxopyridazin-3-ylsulfinyl and benzimidazol-2-ylsulfinyl;

7β-[3-methylsulfinylpropionamido]-7α-methoxy-3acetoxymethyl-3-cephem-4-carboxylic acid and its analogous compounds which have, in place of the 3-methylsulfinyl, their respective substituents such as 2-methylsulfinyl, 3-ethylsulfinyl, 2-methyl-2-methylsulfinyl, 3-phenylsulfinyl, 3-benzylsulfinyl, 2-cyanomethylsulfinyl and 3-cyanomethylsulfinyl;

7β-(methylsulfinylacetamido)-7α-methoxy-3-(1-methyl-1H-tetrazol-5-yl)thiomethyl-3-cephem-4-carboxylic acid and its analogous compounds which have, in place of the methylsulfinyl, their respective substituents such as trifluoromethylsulfinyl, 2,2,2-trifluoroethylsulfinyl, cyanomethylsulfinyl, phenylsulfinyl, ethylsulfinyl, 2-thienylsulfinyl, 2-thienylmethylsulfinyl, 4-pyridylsulfinyl, 1,3,4-thiadiazol-2-ylsulfinyl, 5-methyl-1,3,4-thiadiazol-2-ylsulfinyl, 2-furylsulfinyl and 1-methyl-1H-tetrazol-5-ylsulfinyl;

7β-(methylsulfinylacetamido)-7α-methoxy-3-carbamoyloxymethyl-3-cephem-4-carboxylic acid and its analogous compounds which have, in place of the methylsulfinyl, their respective substituents such as propargylsulfinyl, azidomethylsulfinyl, 4-hydroxyphenylsulfinyl, 2-thienylsulfinyl, 3-thienylsulfinyl, 2-carboxyphenylsulfinyl, N-oxo-4-pyridylsulfinyl, 1,3,4-triazol-5-ylsulfinyl and imidazol-2-ylsulfinyl;

7β-(phenylsulfinylacetamido)-7α-methoxy-3-(5-methyl-1,3,4-thiadiazol-2-yl)thiomethyl-3-cephem-4-carboxylic acid and its analogous compounds which have, in place of the 5-methyl-1,3,4-thiadiazol-2-yl, their respective substituents such as 1H-tetrazol-5-yl, 1-ethyl-1H-tetrazol-5-yl, 1,3,4-thiadiazol-2-yl, 1,3,4-oxadiazol-2-yl, 1H-1,3,4-triazol-2-yl and 1H-1,2,3-triazol-5-yl;

7β-(2-thienylsulfinylacetamido)-7α-methoxy-3-(5-methyl-1,3,4-thiadiazol-2-yl)thiomethyl-3-cephem-4-carboxylic acid and its analogous compounds which have, in place of the 5-methyl-1,3,4-thiadiazol-2-yl, their respective substituents such as 1H-tetrazol-5-yl, 1-ethyl-1H-tetrazol-5-yl, 1,3,4-thiadiazol-2-yl, 1,3,4-oxadiazol-2-yl, 1H-1,3,4-triazol-2-yl, 3-methyl-1,2,4-thiadiazol-5-yl, 1H-1,2,3-triazol-5-yl, N-oxopyridin-2-yl, 1-carboxymethyl-1H-tetrazol-5-yl and 6-methyl-1-oxopyridazin-3-yl;

7β-(2-thienylsulfinylacetamido)-7α-methoxy-3-deacetoxycephalosporanic acid;

7β-(2-thienylsulfinylacetamido)-7α-methoxy-3-methoxymethyl-3-cephem-4-carboxylic acid;

7β-(2-thienylsulfinylacetamido)-7α-methoxy-3-methylthiomethyl-3-cephem-4-carboxylic acid; and the like.

These 7α-methoxycephalosporins of the R form represented by the above general formula (I) as such may be employed in the form of a free acid for medical treatment. They may also be converted into their pharmacologically acceptable salts by reaction with such a salt-forming agent that it is generally used in the field of cepharosporins, and may then be employed for medical treatment. As examples of saltforming partners in formation of pharmacologically acceptable salts, there can be mentioned non-toxic cations such as sodium ion, potassium ion and the like; basic amino acids such as arginine, ornithine, lysine, histidine and the like; amines such as N-methylglucamine, diethanolamine, triethanolamine, tris(hydroxymethyl)aminomethane and the like; and the like.

Those 7α-methoxycephalosporins and R form represented by the above general formula (I) may also be esterified in their 4-positioned carboxyl group to convert them into their biologically active ester derivatives. Such ester derivatives may advantageously be those of the kind which is capable of increasing the concentration of the active compound in blood and prolonging the effective period of time. Any classes of ester-forming groups which are generally accpeted in the field of cephalosporins, can be employed. More specifically, examples of ester-forming groups which are effective in the present invention include alkoxymethyl groups such as methoxymethyl, ethoxymethyl, isopropoxymethyl and the like; α-alkoxy-α-substituted methyl groups such as α-methoxyethyl, α-ethoxyethyl and the like; alkylthiomethyl groups such as methylthiomethyl, ethylthiomethyl, isopropylthiomethyl and the like; acyloxymethyl groups such as pivaloyloxymethyl and the like; α-acyloxy-α-substituted methyl groups such as α-acetoxybutyl and the like; and the like.

Still further, the present invention is directed to pharmaceutical compositions incorporating a compound of the above general formula (I) hereof as an essential active component in admixture with a pharmaceutically acceptable non-toxic carrier.

The compounds of the present invention can be orally or parenterally administered in the form of capsule, tablet, injection or the like.

The amount to be administered, that is, the dosage of the active 7α-methoxycephalosporin compound (I) or its pharmacologically acceptable salt or ester should be determined by skilled physicians taking consideration of the ages and weight of patients, kinds and severities of disorders and other factors, but there is usually employed the total daily dosage for adults of about 250 to 2,000 mg., preferably in multiple doses such as three or four times a day, while larger total daily dosages may be effectively employed in some cases.

The following examples illustrate the present invention in more detail, but are not to be construed as limiting the scope of the present invention.

In an antimicrobial spectrum, a minimum inhibitory concentration (MIC) against a bacterium is expressed in terms of μg/ml.

EXAMPLE 1

7β-(Methylsulfinylacetamido)-7α-methoxy-3-acetoxymethyl-3-cephem-4-carboxylic acid of the R form 1.2 g of methylsulfinylacetic acid of the R form were added to 10 ml of an acetone solution containing 1 g of triethylamine. To the mixture were dropwise added 1.1 g of ethyl chloroformate at 0° to 20° C. with stirring and then the mixture was stirred at 0° to 20° C. for 30 minutes. To the mixed acid anhydride solution obtained was added a cooled solution (−10° C.) of 4.7 g of benzhydryl 7β-amino-7α-methoxycephalosporanate in 40 ml of an acetone solution containing 1 g of triethylamine and the mixture was vigorously stirred at 0° C. for 30 minutes. Most of the acetone in the thus obtained reaction mixture was evaporated at room temperature under reduced pressure. To the residue were added 100 ml of ethyl acetate. The resulting ethyl acetate solution was washed twice with 20 ml of an aqueous 5% by weight sodium hydrogencarbonate solution cooled with ice, once with 10 ml of water, twice with 20 ml of an aqueous 0.5 N hydrogen chloride solution and once with 10 ml of water. The so washed ethyl acetate solution was dried with sodium sulfate and the ethyl acetate was evaporated under reduced pressure to precipitate the intended compound in the form of benzhydryl ester thereof. Yield: 3.1 g.

1 g of the thus obtained ester compound and 500 mg of anisole were dissolved in 20 ml of trifluoroacetic acid cooled with ice. The mixture was kept at 0° to 5° C. for 30 minutes to obtain the intended compound in the form of free acid. The trifluoroacetic acid and the anisole were evaporated under reduced pressure. To the residue were added 50 ml of water and the pH was adjusted to 7.5 with an aqueous 2 N sodium hydroxide solution to dissolve the product. The so obtained solution was washed with ethyl acetate. The aqueous layer was acidified with an aqueous 2 N hydrogen chloride solution to precipitate the intended compound. Yield: 0.6 g.

Melting point: 125° C. (with decomposition)

EXAMPLE 2

Pivaloyloxymethyl 7β-(methylsulfinylacetamido)-7α-methoxy-3-acetoxymethyl-3-cephem-4-carboxylate of the R form 20 millimoles of chloromethyl pivalate were added to a solution composed of 10 millimoles of the product obtained according to the method described in Example 1, 0.4 ml of an aqueous 5% by weight sodium iodide solution and 170 ml of acetone. To the resulting mixture were added 2 g (20 millimoles) of triethylamine was added. The mixture was stirred for 10 hours and refluxed under heating for one hour. Then, the reaction mixture was cooled to room temperature and concentrated under reduced pressure. To the residue were added 100 ml of ethyl acetate and 20 ml of an aqueous 5% by weight sodium hydrogencarbonate, and then extraction was conducted. The organic layer was dried with sodium sulfate and the solvent employed for the extraction was evaporated to obtain a crude product. Ether was added to the crude product and the mixture was ground to obtain a powder of the intended compound. Yield: 2.3 g.

Melting point: 116°∼118° C. (with decomposition)

EXAMPLE 3

Potassium 7β-(methylsulfinylacetamido)-7α-methoxy-3-acetoxymethyl-3-cephem-4-carboxylate of the R form 1 millimole of the compound obtained in Example 1 was dissolved in 10 ml of an aqueous 0.1 N potassium hydroxide solution. The solution was freeze-dried to obtain the intended compound.

Melting point: 136°–143° C. (with decomposition)

EXAMPLE 4

7β-(Phenylsulfinylacetamido)-7α-methoxy-3-acetoxymethyl-3-cephem-4-carboxylic acid of the R-form 3.7 g (20 millimoles) of phenylsulfinylacetic acid ($[\alpha]_D^{20}$: +183°, C=1.00, in ethanol) were added to 80 ml of dried acetone. To the resulting mixture were added 2.8 ml of triethylamine and 5 drops of N,N-dimethylbenzylamine with stirring and the mixture was cooled to −20° C. To the cooled mixture were added 2.4 g of pivaloyl chloride with stirring. After further stirring the mixture at −20° C. for 30 minutes, a mixture of 9.4 g of benzhydryl 7β-amino-7α-methoxycephalosporanate, 2.8 ml of triethylamine and 40 ml of anhydrous acetone were added thereto at a stroke with vigorously stirring at −20° C. Then, the mixture was stirred at −20° C. for 30 minutes, at 0° C. for one hour and then at room temperature for 2 hours. Most of the acetone in the thus obtained reaction mixture was evaporated at room temperature under reduced pressure. To the residue was added 200 ml of ethyl acetate. The resulting ethyl acetate solution was washed twice with 40 ml of an aqueous 5% by weight sodium hydrogencarbonate solution cooled with ice, once with 20 ml of water, twice with 40 ml of an aqueous 0.5 N hydrogen chloride solution and once with 20 ml of water. The so washed ethyl acetate solution was dried with sodium sulfate and the ethyl acetate was evaporated under reduced pressure to precipitate the intended compound in the form of benzhydryl ester thereof. Yield: 3.1 g.

1 g of the thus obtained ester compound and 500 mg of anisole were dissolved in 20 ml of trifluoroacetic acid cooled with ice. The mixture was kept at 0° to 5° C. for 30 minutes to obtain the intended compound in the form of free acid. The trifluoroacetic acid and the anisole were evaporated under reduced pressure. To the residue were added 50 ml of water and the pH was adjusted to 7.5 with an aqueous 2 N sodium hydroxide solution to dissolve the product. The so obtained solution was washed with ethyl acetate. The aqueous layer was acidified with an aqueous 2 N hydrogen chloride solution to precipitate the intended compound. Yield: 0.4 g.

Melting point: 152°–154° (with decomposition)

EXAMPLE 5

7β-(Phenylsulfinylacetamido)-7α-methoxy-3-(2-methyl-1,3,4-thiadiazol-5-ylthiomethyl)-3-cephem-4-carboxylic acid of the R form To 10 ml of a phosphoric acid buffer solution (pH 6.4) was added a solution composed of 0.5 g of the compound obtained in Example 4, 0.1 g of sodium hydrogencarbonate and 0.15 g of 5-mercapto-2-methyl-1,3,4-thiadiazole. The mixture was stirred at 60° C. for 6 hours. The thus obtained reaction mixture was cooled to room temperature, the pH was adjusted to 3 with an aqueous 2 N hydrochloric acid solution and then extraction was conducted with 50 ml of ethyl acetate. The ethyl acetate layer was washed with 50 ml of an aqueous saturated sodium chloride solution and dried with sodium sulfate, and the solvent employed for the extraction was evaporated under reduced pressure to precipitate the intended compound. Yield: 0.23 g.

Melting point: 163°–165° C. (with decomposition)

EXAMPLES 6 TO 12

Substantially the same procedures as described in Example 5 were repeated by using a compound indicated in Item (I) below, instead of 5-mercapto-2-methyl-1,3,4-thiadiazole, to obtain the intended compound of the R form as indicated in Item (II) below.

EXAMPLE 6

(I) 1-Oxopyridine-2-thiol
(II) 7β-(Phenylsulfinylacetamido)-7α-methoxy-3-(1-oxopyridin-2-ylthiomethyl)-3-cephem-4-carboxylic acid of the R form Melting point: 125°–130° C. (with decomposition)

EXAMPLE 7

(I) 3-Methyl-1,2,4-thiadiazole-5-thiol
(II) 7β-(Phenylsulfinylacetamido)-7α-methoxy-3-(3-methyl-1,2,4-thiadiazol-5-ylthiomethyl)-3-cephem-4-carboxylic acid of the R form Melting point: 118°–122° C. (with decomposition)

EXAMPLE 8

(I) 1-Methyl-1H-tetrazole-5-thiol
(II) 7β-(Phenylsulfinylacetamido)-7α-methoxy-3-(1-methyl-1H-tetrazole-5-ylthiomethyl)-3-cephem-4-carboxylic acid of the R form Melting point: 108°–115° C. (with decomposition)

EXAMPLE 9

(I) 1H-Tetrazole-5-thiol
(II) 7β-(Phenylsulfinylacetamido)-7α-methoxy-3-(1H-tetrazol-5-ylthiomethyl)-3-cephem-4-carboxylic acid of the R from Melting point: 120°–125° C. (with decomposition)

EXAMPLE 10

(I) 1H-1,2,3-Triazole-5-thiol
(II) 7β-(Phenylsulfinylacetamido)-7α-methoxy-3-(1H-1,2,3-triazol-5-ylthiomethyl)-3-cephem-4-carboxylic acid of the R form Melting point: 106°–110° C. (with decomposition)

EXAMPLE 11

(I) 1,3,4-Thiadiazole-2-thiol
(II) 7β-(Phenylsulfinylacetamido)-7α-methoxy-3-(1,3,4-thiadiazol-2-ylthiomethyl)-3-cephem-4-carboxylic acid of the R form Melting point: 134°–140° C. (with decomposition)

EXAMPLE 12

(I) Pyridine
(II) 7β-(Phenylsulfinylacetamido)-7α-methoxy-3-(1-prydiniummethyl)-3-cephem-4-carboxylate of the R form Melting point: 155°–159° C. (with decomposition)

EXAMPLE 13

7β-(2-Thienylsulfinylacetamido)-7α-methoxy-3-carbamoyloxymethyl-3-cephem-4-carboxylic acid of the R form 1.9 g of 2-thienylsulfinylacetic acid of the R form ($[\alpha]_D^{22}$: +33.5°, C=1, in ethanol) were added to 10 ml of an acetone solution containing 1.01 g of triethylamine and reacted with 1.1 g of ethyl chloroformate at 0° to 20° C. for 30 minute to obtain a mixed acid anhydride.

To the resulting solution containing the mixed acid anhydride obtained was added a cooled solution (−10° C.) of 4.7 g of benzhydryl 7β-amino-7α-methoxy-3-carbamoyloxymethyl-3-cephem-4-carboxylate in 40 ml of an acetone solution containing 1 g of triethylamine and the mixture was vigorously stirred at 0° C. for 45 minutes. The acetone in the thus obtained reaction mixture was all evaporated at room temperature under reduced pressure.

To the residue was added 100 ml of ethyl acetate. The resulting ethyl acetate solution was washed twice with 20 ml of an aqueous 5% by weight sodium hydrogencarbonate solution cooled with ice, once with 10 ml of water, twice with 20 ml of an aqueous 0.5 N hydrogen chloride solution and once with 10 ml of water. The so washed ethyl acetate solution was dried with sodium sulfate and the ethyl acetate was evaporated under reduced pressure to precipitate the intended compound in the form of benzhydryl ester thereof. Yield: 4.8 g.

1 g of the thus obtained ester compound and 500 mg of anisole were dissolved in 20 ml of trifluoroacetic acid cooled with ice. The mixture was kept at 0° to 5° C. for 30 minutes to obtain the intended compound in the form of free acid. The trifluoroacetic acid and the anisole were evaporated under reduced pressure. To the residue was added 50 ml of water and the pH was adjusted to 7.5 with an aqueous 2 N sodium hydroxide solution to dissolve the product. The so obtained solution was washed with ethyl acetate. The aqueous layer was acidified with an aqueous 2 N hydrogen chloride solution to precipitate the intended compound. Yield: 0.4 g.

Melting point: 163°–165° C. (with decomposition)

EXAMPLE 14

Substantially the same procedures as described in Example 13 were repeated except that benzhydryl 7β-amino-7α-methoxy-3-methoxymethyl-3-cephem-4-carboxylate was used instead of benzhydryl 7β-amino-7α-methoxy-3-carbamoyloxymethyl-3-cephem-4-carboxylate. 7β-(2-Thienylsulfinylacetamido)-7α-methoxy-3-methoxymethyl-3-cephem-4-carboxylic acid of the R form in the sulfinyl group was obtained in the form of powder.

Melting point: 115°–120° C. (with decomposition)

EXAMPLES 15 TO 19

Substantially the same procedures as described in Example 1 were repeated except that a carboxylic acid of the R form as indicated in Item (I) below was used instead of methylsulfinylacetic acid of the R form, to obtain an intended compound of the R form as indicated in Item (II) below.

EXAMPLE 15

(I) Trifluoromethylsulfinylacetic acid of the R form
(II) 7β-(Trifluoromethylsulfinylacetamido)-7α-methoxy-3-acetoxymethyl-3-cephem-4-carboxylic acid of the R form Melting point: 125°–128° C. (with decomposition)

EXAMPLE 16

(I) Cyanomethylsulfinylacetic acid of the R form
(II) 7β-(Cyanomethylsulfinylacetamido)-7α-methoxy-3-acetoxymethyl-3-cephem-4-carboxylic acid of the R form Melting point: 118°–124° C. (with decomposition)

EXAMPLE 17

(I) 1-Methyl-1H-tetrazol-5-ylsulfinylacetic acid of the R form
(II) 7β-(1-Methyl-1H-tetrazol-5-ylsulfinylacetamido)-7α-methoxy-3-acetoxymethyl-3-cephem-4-carboxylic acid of the R form Melting point: 130°–136° C. (with decomposition)

EXAMPLE 18

(I) Propargylsulfinylacetic acid of the R form
(II) 7β-(Propargylsulfinylacetamido)-7α-methoxy-3-acetoxymethyl-3-cephem-4-carboxylic acid of the R form Melting point: 108°–120° C. (with decomposition)

EXAMPLE 19

(I) 3-Methylsulfinylpropionic acid of the R form
(II) 7β-(3-Methylsulfinylpropionamido)-7α-methoxy-3-acetoxymethyl-3-cephem-4-carboxylic acid of the R form

EXAMPLE 20

Substantially the same procedures as described in Example 4 were repeated except that 2-thienylsulfinylacetic acid of the R form ($[\alpha]_D^{22}$: +33.5°, C=1, in ethanol) was used instead of phenylsulfinylacetic acid of the R form, to obtain 7β-(2-thienylsulfinylacetamido)-7α-methoxy-3-acetoxymethyl-3-cephem-4-carboxylic acid of the R form.

Melting point: 140°–147° C. (with decomposition)

EXAMPLE 21

7β-(2-Thienylsulfinylacetamido)-7α-methoxy-3-(1-methyl-1H-tetrazol-5-ylthiomethyl)-3-cephem-4-carboxylic acid of the R form was prepared by reacting 7β-(2-thienylsulfinylacetamido)-7α-methoxy-3-acetoxymethyl-3-cephem-4-carboxylic acid of the R form obtained in Example 20 with 1-methyl-1H-tetrazole-5-thiol in the same manner as described in Example 5. After completion of the reaction, substantially the same procedures as described in Example 5 were repeated.

Melting point: 129°–135° C. (with decomposition)

Minimum inhibitory concentrations of the obtained compound against various gram-positive bacteria and gram-negative bacteria are shown below. For comparison, MIC data of cefazolin, cephalothin and A as indicated below are also shown below.

Cefazolin: 7-(1H-Tetrazol-1-ylacetamido)-3-(5-methyl-1,3,4-thiadiazol-2-ylthiomethyl)-3-cephem-4-carboxylic acid Cephalothin: 7-(2-Thienylacetamido)-3-acetoxymethyl-3-cephem-4-carboxylic acid A: 7-(2-Thienylsulfinylacetamido)-3-(1-methyl-1H-tetrazol-5-ylthiomethyl)-3-cephem-4-carboxylic acid of the R form

| | MIC (μg/ml) | | | |
|---|---|---|---|---|
| | | Compatative compounds | | |
| Bacterium | Example 21 | Cefazolin | Cephalothin | A |
| Staphylococcus aureus, ATCC 6538 P | 0.8 | ≦0.2 | ≦0.2 | ≦0.2 |
| Staphylococcus aureus, ATCC MS 27 | 0.8 | 0.8 | 0.4 | 0.4 |
| Escherichia coli, NIHJ | 1.6 | 1.6 | 6.3 | 0.8 |
| Escherichia coli, 0205 | 3.1 | 12.5 | >100 | 25 |
| Salmonella enteritidis gaertner | ≦0.2 | 1.6 | 1.6 | ≦0.2 |
| Klebsiella pheumoniae, ATCC 10031 | ≦0.2 | 1.6 | 0.8 | ≦0.2 |
| Proteus mirabilis | 0.8 | 3.1 | 6.3 | 0.8 |
| Proteus rettgeri, ACR | 6.3 | >100 | >100 | 25 |
| Proteus morganii 0239 | 12.5 | >100 | >100 | >100 |
| Enterobacter cloacae GN 336 | 25 | >100 | >100 | 100 |
| Citrobacter freundii GN 346 | 100 | >100 | >100 | >100 |

EXAMPLE 22

Substantially the same procedures as described in Example 21 were repeated except that a heterocyclic thiol and an alkylthiol as indicated in Item (I) below were respectively used instead of 1-methyl-1H-tetrazole-5-thiol, to obtain a compound of the R form as indicated in Item (II) below.

22-a (I) 5-Methyl-1,3,4-thiadiazole-2-thiol
(II) 7β-(2-Thienylsulfinylacetamido)-7α-methoxy-3-(5-methyl-1,3,4-thiadiazol-2-ylthiomethyl)-3-cephem-4-carboxylic acid of the R form
Melting point: 125°–136° C. (with decomposition)

22-b (I) 1H-Tetrazole-5-thiol
(II) 7β-(2-Thienylsulfinylacetamido)-7α-methoxy-3-(1H-tetrazol-5-ylthiomethyl)-3-cephem-4-carboxylic acid of the R form
Melting point: 135°–140° C. (with decomposition)

22-c (I) 3-Methyl-1,2,4-thiadiazole-5-thiol
(II) 7β-(2-Thienylsulfinylacetamido)-7α-methoxy-3-(3-methyl-1,2,4-thiadiazol-5-ylthiomethyl)-3-cephem-4-carboxylic acid of the R form
Melting point: 140°–146° C. (with decomposition)

22-d (I) 1,3,4-Thiadiazole-2-thiol
(II) 7β-(2-Thienylsulfinylacetamido)-7α-methoxy-3-(1,3,4-thiadiazol-2-ylthiomethyl)-3-cephem-4-carboxylic acid of the R form
Melting point: 120°–135° C. (with decomposition)

22-e (I) 1,3,4-Oxadiazole-2-thiol
(II) 7β-(2-Thienylsulfinylacetamido)-7α-methoxy-3-(1,3,4-oxadiazol-2-ylthiomethyl)-3-cephem-4-carboxylic acid of the R form
Melting point: 141°–145° C. (with decomposition)

22-f (I) 1H-1,3,4-Triazole-2-thiol
(II) 7β-(2-Thienylsulfinylacetamido)-7α-methoxy-3-(1H-1,3,4-triazol-2-ylthiomethyl)-3-cephem-4-carboxylic acid of the R form
Melting point: 131°–133° C. (with decomposition)

22-g (I) 1H-1,2,3-Triazole-5-thiol
(II) 7β-(2-Thienylsulfinylacetamido)-7α-methoxy-3-(1H-1,2,3-triazol-5-ylthiomethyl)-3-cephem-4-carboxylic acid of the R form
Melting point: 125°–132° C. (with decomposition)

22-h (I) 1-Ethyl-1H-tetrazole-5-thiol
(II) 7β-(2-Thienylsulfinylacetamido)-7α-methoxy-3-(1-ethyl-1H-tetrazol-5-ylthiomethyl)-3-cephem-4-carboxylic acid of the R form
Melting point: 131°–138° C. (with decomposition)

22-i (I) N-Oxopyridine-2-thiol
(II) 7β-(2-Thienylsulfinylacetamido)-7α-methoxy-3-(N-oxopyridin-2-ylthiomethyl)-3-cephem-4-carboxylic acid of the R form
Melting point: 118°–125° C. (with decomposition)

22-j (I) 1-Carboxymethyl-1H-tetrazole-5-thiol
(II) 7β-(2-Thienylsulfinylacetamido)-7α-methoxy-3-(1-carboxymethyl-1H-tetrazol-5-ylthiomethyl)-3-cephem-4-carboxylic acid of the R form
Melting point: 143°–147° C. (with decomposition)

22-k (I) 6-Methyl-1-oxopyridazine-3-thiol
(II) 7β-(2-Thienylsulfinylacetamido)-7α-methoxy-3-(6-methyl-1-oxopyridazin-3-ylthiomethyl)-3-cephem-4-carboxylic acid of the R form
Melting point: 120°–129° C. (with decomposition)

22-l (I) Methylmercaptan
(II) 7β-(2-Thienylsulfinylacetamido)-7α-methoxy-3-methylthiomethyl-3-cephem-4-carboxylic acid of the R form
Melting point: 108°–116° C. (with decomposition)

EXAMPLE 23

Triethylamine was added to a suspension of 3.6 g of 7β-amino-7α-methoxy-3-(1-methyl-1H-tetrazol-5-ylthiomethyl)-3-cephem-4-carboxylic acid in 40 ml of dimethyl formamide so that all of the solid compound was dissolved. To the solution were added 3.1 g of p-nitrophenyl ester of 2-thienylsulfinylacetic acid ($[\alpha]_D^{22}$: +33.5°, C=1, in ethanol) and the resulting solution was stirred at room temperature for 2 hours. The reaction mixture was then concentrated and dried. The so obtained product was gathered and dissolved in an aqueous triethylamine solution. The pH was adjusted to 7. The so adjusted solution was washed with 100 ml of ethyl acetate, and the ethyl acetate layer was removed. The remaining aqueous layer was acidified with an aqueous 2 N hydrogen chloride solution to have a pH value of 2. The thus acidified solution was subjected to extraction with 100 ml of ethyl acetate. The extract was dried with sodium sulfate and concentrated, so that the volume thereof was reduced to ¼. To the concentrated solution were added 1.6 g of a 20% by weight isopropanol solution of sodium 2-ethylhexanoate. Ether was then added thereto. The resulting suspension was subjected to a filtration to obtain sodium 7β-(2-thienylsulfinylacetamido)-7α-methoxy-3-(1-methyl-1H-tetrazol-5-ylthiomethyl)-3-cephem-4-carboxylate of the R form. Yield: 4.1 g Melting point: 155°–158° C. with decomposition
MIC:
*Escherichia coli*, 0205     3.1 μg/ml

EXAMPLE 24

Substantially the same procedures as described in Example 23 were repeated except that a carboxylic acid of the R form as indicated in Item (I) below was used instead of 2-thienylsulfinylacetic acid of the R form, to obtain a sodium salt of a 7α-methoxycephalosporin of the R form as indicated in Item (II) below.

24-a (I) Trifluoromethylsulfinylacetic acid of the R form
(II) 7β-Trifluoromethylsulfinylacetamido-7α-methoxy-3-(1-methyl-1H-tetrazol-5-ylthiomethyl)-3-cephem-4-carboxylic acid of the R form
Melting point: 135°–141° C. (with decomposition)

24-b (I) Methylsulfinylacetic acid of the R form (II) 7β-Methylsulfinylacetamido-7α-methoxy-3-(1-methyl-1H-tetrazol-5-ylthiomethyl)-3-cephem-4-carboxylic acid of the R form
Melting point: 139°-145° C. (with decomposition)

24-c (I) 2,2,2-Trifluoroethylsulfinylacetic acid of the R form
(II) 7β-(2,2,2-Trifluoroethylsulfinylacetamido)-7α-methoxy-3-(1-methyl-1H-tetrazol-5-ylthiomethyl)-3-cephem-4-carboxylic acid of the R form
Melting point: 131°-135° C. (with decomposition)

24-d (I) Cyanomethylsulfinylacetic acid of the R form
(II) 7β-Cyanomethylsulfinylacetamido-7α-methoxy-3-(1-methyl-1H-tetrazol-5-ylthiomethyl)-3-cephem-4-carboxylic acid of the R form
Melting point: 120°-125° C. (with decomposition)

24-e (I) n-Propylsulfinylacetic acid of the R form
(II) 7β-(n-Propylsulfinylacetamido)-7α-methoxy-3-(1-methyl-1H-tetrazol-5-ylthiomethyl)-3-cephem-4-carboxylic acid of the R form
Melting point: 125°-129° C. (with decomposition)

24-f (I) Propargylsulfinylacetic acid of the R form
(II) 7β-Propargylsulfinylacetamido-7α-methoxy-3-(1-methyl-1H-tetrazol-5-ylthiomethyl)-3-cephem-4-carboxylic acid of the R form
Melting point: 108°-114° C. (with decomposition)

24-g (I) Azidomethylsulfinylacetic acid of the R form
(II) 7β-Azidomethylsulfinylacetamido-7α-methoxy-3-(1-methyl-1H-tetrazol-5-ylthomethyl)-3-cephem-4-carboxylic acid of the R form
Melting point: 120°-124° C. (with decomposition)

24-h (I) Phenylsulfinylacetic acid of the R form
(II) 7β-Phenylsulfinylacetamido-7α-methoxy-3-(1-methyl-1H-tetrazol-5-ylthiomethyl)-3-cephem-4-carboxylic acid of the R form
Melting point: 161°-168° C. (with decomposition)

24-i (I) 4-Hydroxyphenylsulfinylacetic acid of the R form
(II) 7β-(4-Hydroxyphenylsulfinylacetamido)-7α-methoxy-3-(1-methyl-1H-tetrazol-5-ylthiomethyl)-3-cephem-4-carboxylic acid of the R form
Melting point: 158°-162° C. (with decomposition)

24-j (I) 4-Chlorophenylsulfinylacetic acid of the R form
(II) 7β-(4-Chlorophenylsulfinylacetamido)-7α-methoxy-3-(1-methyl-1H-tetrazol-5-ylthiomethyl)-3-cephem-4-carboxylic acid of the R form
Melting point: 145°-152° C. (with decomposition)

24-k (I) 3-Thienylsulfinylacetic acid of the R form
(II) 7β-(3-Thienylsulfinylacetamido)-7α-methoxy-3-(1-methyl-1H-tetrazol-5-ylthiomethyl)-3-cephem-4-carboxylic acid of the R form
Melting point: 162°-167° C. (with decomposition)

24-l (I) 2-Carboxyphenylsulfinylacetic acid of the R form
(II) 7β-(2-Carboxyphenylsulfinylacetamido)-7α-methoxy-3-(1-methyl-1H-tetrazol-5-ylthiomethyl)-3-cephem-4-carboxylic acid of the R form
Melting point: 158°-165° C. (with decomposition)

24-m (I) 2-Aminomethylphenylsulfinylacetic acid of the R form
(II) 7β-(2-Aminomethylphenylsulfinylacetamido)-7α-methoxy-3-(1-methyl-1H-tetrazol-5-ylthiomethyl)-3-cephem-4-carboxylic acid of the R form
Melting point: 147°-153° C. (with decomposition)

24-n (I) 4-Pyridylsulfinylacetic acid of the R form
(II) 7β-(4-Pyridylsulfinylacetamido)-7α-methoxy-3-(1-methyl-1H-tetrazol-5-ylthiomethyl)-3-cephem-4-carboxylic acid of the R form
Melting point: 180°-185° C. (with decomposition)

24-o (I) N-Oxo-4-pyridylsulfinylacetic acid of the R form
(II) 7β-(N-Oxo-4-pyridylsulfinylacetamido)7α-methoxy-3-(1-methyl-1H-tetrazol-5-ylthiomethyl)-3-cephem-4-carboxylic acid of the R form
Melting point: 140°-144° C. (with decomposition)

24-p (I) 5-Methyl-1,3,4-thiadiazol-2-ylsulfinylacetic acid of the R form
(II) 7β-(5-Methyl-1,3,4-thiadiazol-2-ylsulfinylacetamido)-7α-methoxy-3-(1-methyl-1H-tetrazol-5-ylthiomethyl)-3-cephem-4-carboxylic acid of the R form
Melting point: 152°-157° C. (with decomposition)

24-q (I) 1,3,4-Thiadiazol-2-ylsulfinylacetic acid of the R form
(II) 7β-(1,3,4-Thiadiazol-2-ylsulfinylacetamido)-7α-methoxy-3-(1-methyl-1H-tetrazol-5-ylthiomethyl)-3-cephem-4-carboxylic acid of the R form
Melting point: 175°-177° C. (with decomposition)

24-r (I) 1-Methyl-1H-tetrazol-5-ylsulfinylacetic acid of the R form
(II) 7β-(1-Methyl-1H-tetrazol-5-ylsulfinylacetamido)-7α-methoxy-3-(1-methyl-1H-tetrazol-5-ylthiomethyl)-3-cephem-4-carboxylic acid of the R form
Melting point: 160°-169° C. (with decomposition)

24-s (I) 2-Thienylmethylsulfinylacetic acid of the R form
(II) 7β-(2-Thienylmethylsulfinylacetamido)-7α-methoxy-3-(1-methyl-1H-tetrazol-5-ylthiomethyl)-3-cephem-4-carboxylic acid of the R form
Melting point: 148°-158° C. (with decomposition)

24-t (I) 6-Methyl-1-oxopyridazin-3-ylsulfinylacetic acid of the R form
(II) 7β-(6-Methyl-1-oxopyridazin-3-ylsulfinylacetamido)-7α-methoxy-3-(1-methyl-1H-tetrazol- 5-ylthiomethyl)-3-cephem-4-carboxylic acid of the R form Melting point: 151°–153° C. (with decomposition)

24-u (I) Benzimidazol-2-ylsulfinylacetic acid of the R form
(II) 7β-(Benzimidazol-2-ylsulfinylacetamido)-7α-methoxy-3-(1-methyl-1H-tetrazol-5-ylthiomethyl)-3-cephem-4-carboxylic acid of the R form Melting point: 148°–154° C. (with decomposition)

24-v (I) 2-Furylsulfinylacetic acid of the R form
(II) 7β-(2-Furylsulfinylacetamido)-7α-methoxy-3-(1-methyl-1H-tetrazol-5-ylthiomethyl)-3-cephem-4-carboxylic acid of the R form Melting point: 140°–145° C. (with decomposition)

EXAMPLE 25

Substantially the same procedures as described in Example 4 were repeated except that 0.02 mole of a carboxylic acid of the R form as indicated in Item (I) below was used instead of phenylsulfinylacetic acid of the R form, to obtain a 7α-methoxycephalosporin of the R form as indicated in Item (II) below.

25-a (I) n-Octylsulfinylacetic acid of the R form
(II) 7β-(n-Octylsulfinylacetamido)-7α-methoxy-3-acetoxymethyl-3-cephem-4-carboxylic acid of the R form Melting point: 128°–133° C. (with decomposition)

25-b (I) Benzylsulfinylacetic acid of the R form
(II) 7β-Benzylsulfinylacetamido-7α-methoxy-3-acetoxymethyl-3-cephem-4-carboxylic acid of the R form Melting point: 125°–127° C. (with decomposition)

25-c (I) 3-(p-Methoxyphenyl)propylsulfinylacetic acid of the R form
(II) 7β-[3-(p-Methoxyphenyl)propylsulfinylacetamido]-7α-methoxy-3-acetoxymethyl-3-cephem-4-carboxylic acid of the R form Melting point: 131°–137° C. (with decomposition)

25-d (I) 2-Nitrofuran-5-ylsulfinylacetic acid of the R form
(II) 7β-(2-Nitrofuran-5-ylsulfinylacetamido)-7α-methoxy-3-acetoxymethyl-3-cephem-4-carboxylic acid of the R form Melting point: 138°–141° C. (with decomposition)

25-e (I) 2,4,6-Trifluorophenylsulfinylacetic acid of the R form
(II) 7β-(2,4,6-Trifluorophenylsulfinylacetamido)-7α-methoxy-3-acetoxymethyl-3-cephem-4-carboxylic acid of the R form Melting point: 140°–147° C. (with decomposition)

EXAMPLE 26

Substantially the same procedures as described in Example 23 were repeated except that a compound (the same molar amount as in Example 23) as indicated in Item (I) below was used instead of 7β-amino-7α-methoxy-3-(1-methyl-1H-tetrazol-5-ylthiomethyl)-3-cephem-4-carboxylic acid, to obtain a sodium salt of a 7α-methoxycephalosporin of the R form as indicated in Item (II) below.

26-a (I) 7β-Amino-7α-methoxy-3-{[tetrazolo(4,5-b)pyridazin-6-yl]thiomethyl}-3-cephem-4-carboxylic acid
(II) 7β-(2-Thienylsulfinylacetamido)-7α-methoxy-3-{[tetrazolo(4,5-b)pyridazin-6-yl]thiomethyl}-3-cephem-4-carboxylic acid of the R form Melting point: 170°–177° C. (with decomposition)

26-b (I) 7β-Amino-7α-methoxy-3-(4-allyl-1,2,4-triazol-3-ylthiomethyl)-3-cephem-4-carboxylic acid
(II) 7β(2-Thienylsulfinylacetamido)-7α-methoxy-3-(4-allyl-1,2,4-triazol-3-ylthiomethyl)-3-cephem-4-carboxylic acid of the R form Melting point: 145°–155° C. (with decomposition)

26-c (I) 7β-Amino-7α-methoxy-3-(4-methyl-5-trifluoromethyl-1,2,4-triazol-3-ylthiomethyl)-3-cephem-4-carboxylic acid
(II) 7β-(2-Thienylsulfinylacetamido-7α-methoxy-3-(4-methyl-5-trifluoromethyl-1,2,4-triazol-3-ylthiomethyl)-3-cephem-4-carboxylic acid of the R form Melting point: 159°–165° C. (with decomposition)

26-d (I) 7β-Amino-7α-methoxy-3-(1-methoxymethyl-1H-tetrazol-5-ylthiomethyl)-3-cephem-4-carboxylic acid
(II) 7β-(2-Thienylsulfinylacetamido)-7α-methoxy-3-(1-methoxymethyl-1H-tetrazol-5-ylthiomethyl)-3-cephem-4-carboxylic acid of the R form Melting point: 153°–163° C. (with decomposition)

26-e (I) 7β-Amino-7α-methoxy-3-(5-trifluoromethyl-1,3,4-thiadiazol-2-ylthiomethyl)-3-cephem-4-carboxylic acid
(II) 7β-(2-Thienylsulfinylacetamido)-7α-methoxy-3-(5-trifluoromethyl-1,3,4-thiadiazol-2-ylthiomethyl)-3-cephem-4-carboxylic acid of the R form Melting point: 139°–150° C. (with decomposition)

26-f (I) 7β-Amino-7α-methoxy-3-(5-n-butyl-1,3,4-thiadiazol-2-ylthiomethyl)-3-cephem-4-carboxylic acid
(II) 7β-(2-Thienylsulfinylacetamido)-7α-methoxy-3-(5-n-butyl-1,3,4-thiadiazol-2-ylthiomethyl)-3-cephem-4-carboxylic acid of the R form Melting point: 142°–145° C. (with decomposition)

26-g (I) 7β-Amino-7α-methoxy-3-(5-hydroxymethyl-1,3,4-thiadiazol-2-ylthiomethyl)-3-cephem-4-carboxylic acid
(II) 7β-(2-Thienylsulfinylacetamido)-7α-methoxy-3-(5-hydroxymethyl-1,3,4-thiadiazol-2-ylthiomethyl)-3-cephem-4-carboxylic acid of the R form Melting point: 158°–165° C. (with decomposition)

26-h (I) 7β-Amino-7α-methoxy-3-[5-(2-aminoethyl)-1,3,4-thiadiazol-2-ylthiomethyl]-3-cephem-4-carboxylic acid (II) 7β-(2-Thienylsulfinylacetamido)-7α-methoxy-3-[5-(2-aminoethyl)-1,3,4-thiadiazol-2-ylthiomethyl]-3-cephem-4-carboxylic acid of the R form Melting point: 135°–143° C. (with decomposition)

26-i (I) 7β-Amino-7α-methoxy-3-(1-methylsulfonyl-1H-tetrazol-5-ylthiomethyl)-3-cephem-4-carboxylic acid (II) 7β-(2-Thienylsulfinylacetamido)-7α-methoxy-3-(1-methylsulfonyl-1H-tetrazol-5-ylthiomethyl)-3-cephem-4-carboxylic acid of the R form Melting point: 168°–173° C. (with decomposition)

26-j (I) 7β-Amino-7α-methoxy-3-(1-acetyl-1H-tetrazol-5-ylthiomethyl)-3-cephem-4-carboxylic acid (II) 7β-(2-Thienylsulfinylacetamido)-7α-methoxy-3-(1-acetyl-1H-tetrazol-5-ylthiomethyl)-3-cephem-4-carboxylic acid of the R form Melting point: 155°–160° C. (with decomposition)

26-k (I) 7β-Amino-7α-methoxy-3-[5-(N,N-dimethylamino)-1,3,4-thiadiazol-2-ylthiomethyl]-3-cephem-4-carboxylic acid (II) 7β-(2-Thienylsulfinylacetamido)-7α-methoxy-[5-(N,N-dimethylamino)-1,3,4-thiadiazol-2-ylthiomethyl]-3-cephem-4-carboxylic acid of the R form Melting point: 126°–135° C. (with decomposition)

EXAMPLE 27

Substantially the same procedures as described in Example 4 were repeated except that 8.5 g of benzhydryl 7β-amino-7α-methoxy-3-deacetoxycephalosporanate was used instead of benzhydryl 7β-amino-7α-methoxycephalosporanate, to obtain 7β-phenylsulfinylacetamido-7α-methoxy-3-methyl-3-cephem-4-carboxylic acid of the R form.

Melting point: 169°–175° C. (with decomposition)

What is claimed is:

1. A 7α-methoxycephalosporin or its pharmacologically acceptable salts of the formula

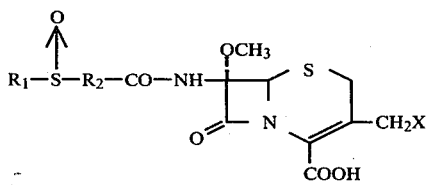

wherein $R_1$ is selected from the group consisting of 2-thienyl, 3-thienyl, 4-pyridyl, N-oxo-2-pyridyl, N-oxo-4-pyridyl, 5-methyl-1,3,4-thiadiazol-2-yl, 1,3,4-thiadiazol-2-yl, 1-methyl-1H-tetrazol-5-yl, 6-methyl-1-oxopyridazin-3-yl, benzimidazol-2-yl, 2-furyl and 2-thienylmethyl;

$R_2$ is methylene; and

X is selected from the group consisting of acetoxy, carbamoyloxy, methoxy, methylthio, 1-methyl-1H-tetrazol-5-ylthio, 5-methyl-1,3,4-thiadiazol-2-ylthio, 1H-tetrazol-5-ylthio, 3-methyl-1,2,4-thiadiazol-5-ylthio, 1,3,4-thiadiazol-2-ylthio, 1,3,4-oxadiazol-2-ylthio, 1H-1,3,4-triazol-2-ylthio, 1H-1,2,3-triazol-5-ylthio, 1-ethyl-1H-tetrazol-5-ylthio, N-oxopyridin-2-ylthio, 1-carboxymethyl-1H-tetrazol-5-ylthio, 5-(N,N-dimethylamino)-1,3,4-thiadiazol-2-ylthio and 6-methyl-1-oxopyridazin-3-ylthio; and wherein said R form means an optical isomer having stereochemically the same structure in the sulfinyl group as that optical isomer of the two sulfinyl group stereoisomers of a compound of the formula (II) which has a positive specific rotation in ethanol:

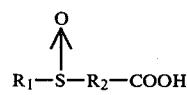

wherein $R_1$ and $R_2$ are the same as defined above.

2. 7β-(2-Thienylsulfinylacetamido)-7α-methoxy-3-acetoxymethyl-3-cephem-4-carboxylic acid of the R form or its pharmacologically acceptable salts.

3. 7β-(2-Thienylsulfinylacetamido)-7α-methoxy-3-(5-methyl-1,3,4-thiadiazol-2-ylthiomethyl)-3-cephem-4-carboxylic acid of the R form or its pharamcologically acceptable salts.

4. 7β-(2-Thienylsulfinylacetamido)-7α-methoxy-3-(1-methyl-1H-tetrazol-5-ylthiomethyl)-3-cephem-4-carboxylic acid of the R form or its pharmacologically acceptable salts.

5. A 7α-methoxycephalosporin or its pharmacologically acceptable salts according to claim 1, wherein $R_1$ is 2-thienyl.

6. A 7α-methoxycephalosporin or its pharmacologically acceptable salts according to claim 1, wherein $R_1$ is 2-furyl.

7. A compound according to claim 1 which is 7β-(2-thienylsulfinylacetamido)-7α-methoxy-3-(1-carboxymethyl-1H-tetrazol-5-ylthiomethyl)-3-cephem-4-carboxylic acid of the R form or its pharmacologically acceptable salts.

8. A compound according to claim 1 which is 7β-(2-furylsulfinylacetamido)-7α-methoxy-3-(1-methyl-1H-tetrazol-5-ylthiomethyl)-3-cephem-4-carboxylic acid of the R form or its pharmacologically acceptable salts.

9. A compound according to claim 1 wherein $R_1$ is thienyl.

10. A compound according to claim 1 wherein the R form is free from its stereoisomer.

* * * * *